US00PP22582P2

(12) United States Plant Patent
Gomez Bullis

(10) Patent No.: US PP22,582 P2
(45) Date of Patent: Mar. 13, 2012

(54) ***NEOREGELIA* PLANT NAMED 'FLIRTING'**

(50) Latin Name: ***Neoregelia macrosephala*×*Neoregelia carolinae***
Varietal Denomination: Flirting

(75) Inventor: Patricia E. Gomez Bullis, Princeton, FL (US)

(73) Assignee: Bullis Bromeliads, Princeton, FL (US)

( * ) Notice: Subject to any disclaimer, the term of this patent is extended or adjusted under 35 U.S.C. 154(b) by 12 days.

(21) Appl. No.: 12/806,819

(22) Filed: Aug. 21, 2010

(51) Int. Cl.
*A01H 5/00* (2006.01)

(52) U.S. Cl. ..... Plt./370

(58) Field of Classification Search ..... Plt./370
See application file for complete search history.

*Primary Examiner* — June Hwu
(74) *Attorney, Agent, or Firm* — C. A. Whealy

(57) ABSTRACT

A new and distinct cultivar of *Neoregelia* plant named 'Flirting', characterized by its upright and outwardly arching growth habit; glossy green-colored lower leaves that are overlain with dark red purple; glossy purple-colored upper leaves; non-fading leaf color under low light levels; and good interiorscape and landscape performance.

1 Drawing Sheet

Botanical designation: *Neoregelia macrosephala*×*Neoregelia carolinae.*

Cultivar denomination: 'FLIRTING'.

BACKGROUND OF THE INVENTION

The present invention relates to a new and distinct cultivar of *Neoregelia* plant, botanically known as *Neoregelia macrosephala*×*Neoregelia carolinae*, and hereinafter referred to by the name 'Flirting'.

The new *Neoregelia* plant is a product of a planned breeding program conducted by the Inventor in Princeton, Fla. The objective of the breeding program is to create new *Neoregelia* plants with uniquely colored leaves.

The new *Neoregelia* plant originated from a cross-pollination made by the Inventor in 2002 in Princeton, Fla. of an unnamed proprietary selection of *Neoregelia macrosephala*, not patented, as the female, or seed, parent with *Neoregelia carolinae* 'Victoria', not patented, as the male, or pollen, parent. The new *Neoregelia* plant was discovered and selected by the Inventor as a single plant within the progeny of the stated cross-pollination in a controlled greenhouse environment in Princeton, Fla. in 2002.

Asexual reproduction of the new *Neoregelia* plant by offsets in a controlled environment in Princeton, Fla. since 2003, has shown that the unique features of this new *Neoregelia* plant are stable and reproduced true to type in successive generations.

SUMMARY OF THE INVENTION

Plants of the new *Neoregelia* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Flirting'. These characteristics in combination distinguish 'Flirting' as a new and distinct cultivar of *Neoregelia:*

1. Upright and outwardly arching growth habit.
2. Glossy green-colored lower leaves that are overlain with dark red purple.
3. Glossy purple-colored upper leaves.
4. Non-fading leaf color under low light levels.
5. Good interiorscape and landscape performance.

Plants of the new *Neoregelia* differ primarily from plants of the female parent selection in leaf color.

Plants of the new *Neoregelia* differ primarily from plants of the male parent, 'Victoria', in durability as plants of the new *Neoregelia* tolerate shipping stress and summer rains better than plants of 'Victoria'.

Plants of the new *Neoregelia* can be compared to plants of the *Neoregelia* 'Medium Rare', not patented. Plants of the new *Neoregelia* grow faster and are more vigorous than plants of 'Medium Rare'. In addition, plants of the new *Neoregelia* tolerate hot and rainy weather better than plants of 'Medium Rare'.

BRIEF DESCRIPTION OF THE PHOTOGRAPHS

The accompanying colored photographs illustrate the overall appearance of the new *Neoregelia* plant showing the colors as true as it is reasonably possible to obtain in colored reproductions of this type. Colors in the photographs may differ slightly from the color values cited in the detailed botanical description which accurately describe the colors of the new *Neoregelia* plant.

The photograph at the bottom of the sheet is a side perspective view of a typical flowering plant of 'Flirting' grown in a container.

The photograph at the top of the sheet is a top perspective view of a typical flowering plant of 'Flirting'.

DETAILED BOTANICAL DESCRIPTION

The aforementioned photographs and following observations, measurements and values describe flowering plants grown during the spring in 15-cm containers in a polypropylene-covered greenhouse in Princeton, Fla. under commercial *Neoregelia* production practices. During the production of the plants, day temperatures ranged from 10° C. to 32° C., night temperatures ranged from 7° C. to 32° C. and light levels averaged 3,200 foot-candles. Plants were one year old when the photographs and description were taken. In the following description, color references are made to The Royal Horticultural Society Colour Chart, 2007 Edition, except where general terms of ordinary dictionary significance are used.

Botanical classification: *Neoregelia macrosephala*×*Neoregelia carolinae* 'Flirting'.

Parentage:

*Female, or seed, parent.*—Unnamed proprietary selection of *Neoregelia macrosephala*, not patented.

*Male, or pollen, parent.*—*Neoregelia carolinae* 'Victoria', not patented.

Propagation:

*Type.*—By offsets.

*Time to initiate roots, summer.*—About 30 days at 28° C. to 30° C.

*Time to initiate roots, winter.*—About 45 days at 18° C. to 22° C.

*Time to produce a rooted young plant, summer.*—About three months at 28° C. to 30° C.

*Time to produce a rooted young plant, winter.*—About four months at 18° C. to 22° C.

*Root description.*—Medium in thickness, fibrous; yellow to tan in color.

*Rooting habit.*—Moderately freely branching; medium density.

Plant description:

*Plant form/growth habit.*—Upright and outwardly arching growth habit; rosette leaves are erect when young, becoming outwardly arching with development; plants readily produce uniform offsets; vigorous growth habit.

*Plant height.*—About 18.5 cm.

*Plant diameter or spread.*—About 50 cm.

*Internode length.*—About 4 mm.

*Stem texture.*—Smooth, glabrous.

*Stem color.*—Close to NN155C.

Foliage description:

*Arrangement.*—Rosette, spiral phyllotaxis; simple; sessile, clasping.

*Shape.*—Oblong.

*Apex.*—Cuspidate.

*Base.*—Truncate.

*Margin.*—Serrate, spinose.

*Length.*—About 34.5 cm.

*Width, mid-section.*—About 6.2 cm.

*Width, base.*—About 10.4 cm.

*Texture.*—Smooth, glabrous; leathery; longitudinally ribbed.

*Luster.*—Glossy.

*Venation pattern.*—Parallel.

*Color.*—Lower leaves, upper surface: Ground color, close to N137A tinted with 70A and 71A; towards the base, close to N77D; venation, close to N137A. Lower leaves, lower surface: Close to 183C tinted with close to N137D; towards the base, close to 59C; venation, close to 183C. Upper leaves, upper and lower surfaces: Close to N77B; towards the base, close to 156C; venation, close to N77B.

Inflorescence description:

*Inflorescence form.*—Terminal flat-topped compact corymb located inside the leaf rosette; about 75 flowers develop per inflorescence.

*Time to flower.*—Plants begin flowering about nine to eleven weeks after planting; plants flower naturally during the spring in Florida.

*Flower longevity.*—Individual flowers last about one day on the plant; flowers persistent.

*Fragrance.*—None detected.

*Inflorescence length.*—About 6 cm.

*Inflorescence diameter.*—About 3.4 cm.

*Flower size.*—Length: About 5.2 cm. Diameter: About 8 mm.

*Flower buds.*—Length: About 3.9 cm. Diameter: About 7 mm. Shape: Elongated oblong. Color: Close to 91B.

*Petals.*—Quantity per flower: Three in a single whorl. Shape: Oblanceolate. Apex: Acuminate. Base: Truncate. Margin: Entire. Length: About 4.2 cm. Width: About 8 mm. Texture: Smooth, glabrous. Color: When opening and fully opened, upper surface: Close to NN155D; towards the apex, close to 91A. When opening and fully opened, lower surface: Close to NN155D; towards the apex, close to 91B.

*Flower bracts.*—Quantity per flower: One. Shape: Elliptical. Length: About 3.9 cm. Width: About 1.8 cm. Texture: Membraneous. Color: Close to 157D.

*Sepals.*—Quantity per flower: Three in a single whorl. Shape: Oblanceolate. Apex: Acuminate. Base: Truncate. Margin: Entire. Length: About 2.7 cm. Width: About 8 mm. Texture: Smooth, glabrous. Color, upper surface: Close to 146C. Color, lower surface: Close to 146D.

*Peduncles.*—Length: About 7 mm. Diameter: About 1.4 cm. Strength: Strong. Aspect: Typically erect. Texture: Smooth, glabrous. Color: Close to NN155D.

*Pedicels.*—Length: About 9 mm. Diameter: About 5 mm. Strength: Strong. Aspect: Typically erect to somewhat outward and curving upright. Texture: Smooth, glabrous. Color: Close to NN155B.

*Stamens.*—Quantity per flower: Six. Filament length: About 2.3 cm; partially adnate to the petals. Filament color: Close to NN155D. Anther shape: Lanceolate. Anther length: About 6 mm. Anther color: Close to 158B. Pollen amount: Scarce. Pollen color: Close to 158B.

*Pistils.*—Quantity per flower: One. Pistil length: About 3.7 cm. Stigma shape: Oval, elongated. Stigma color: Close to 155C. Style length: About 2.3 cm. Style color: Close to NN155C. Ovary color: Close to NN155B.

*Fruit/seed.*—Fruit and seed production have not been observed on plants of the new *Neoregelia*.

Temperature tolerance: Plants of the new *Neoregelia* have been observed to tolerate temperatures ranging from about 2° C. to about 37° C.

Interior & garden performance: Plants of the new *Neoregelia* have been observed to have good postproduction longevity under interior conditions and to have good garden performance. Plants of the new *Neoregelia* have been observed to tolerate summer rains.

Disease/pest resistance: Resistance to pathogens and pests common to *Neoregelia* plants has not been observed.

It is claimed:

1. A new and distinct *Neoregelia* plant named 'Flirting' as illustrated and described.

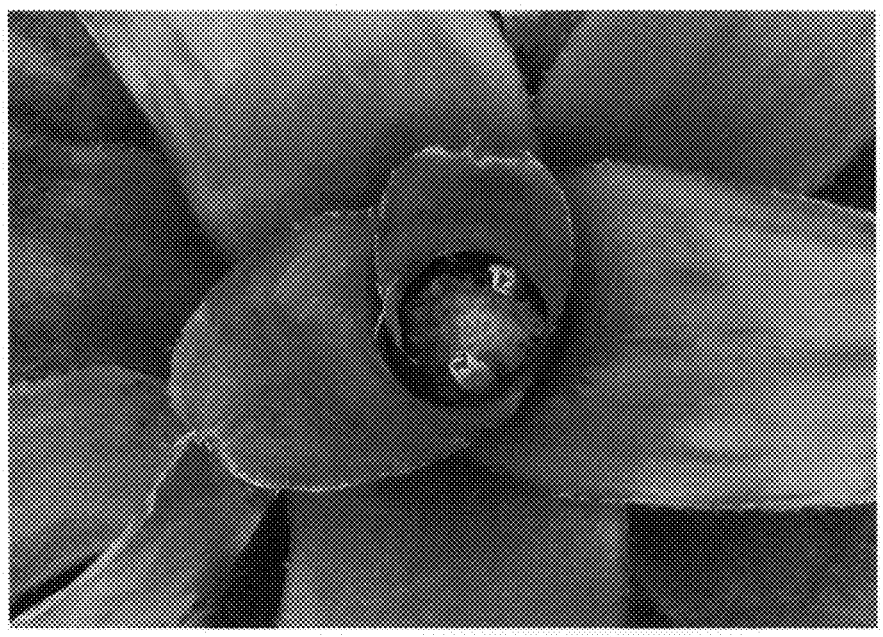
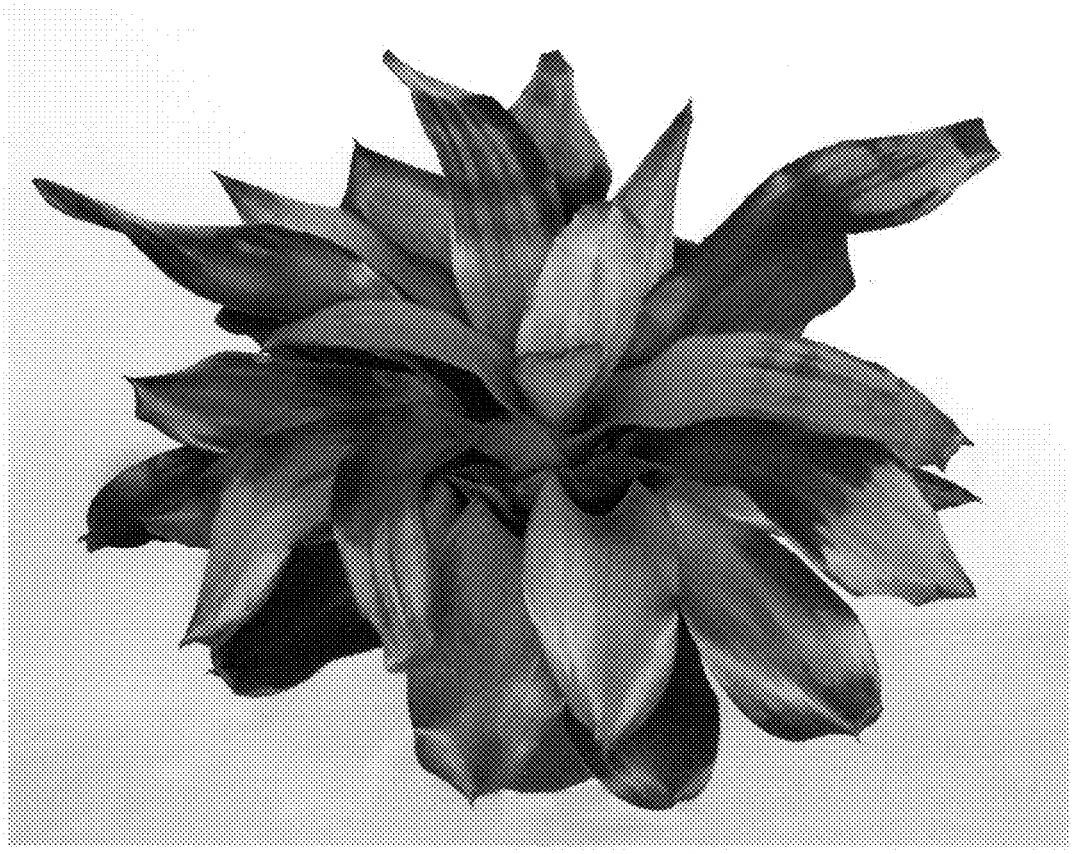

* * * * *